(12) United States Patent
Roberts et al.

(10) Patent No.: US 11,951,235 B2
(45) Date of Patent: Apr. 9, 2024

(54) DEVICE FOR REDUCING ODOR IN ATHLETIC APPAREL STORAGE

(71) Applicant: DeoTech, LLC, Palatine, IL (US)

(72) Inventors: Drake Roberts, Palatine, IL (US); Anthony Tamras, Island Lake, IL (US)

(73) Assignee: DEO COMPANY LLC, Palatine, IL (US)

( * ) Notice: Subject to any disclaimer, the term of this patent is extended or adjusted under 35 U.S.C. 154(b) by 895 days.

(21) Appl. No.: 17/005,689

(22) Filed: Aug. 28, 2020

(65) Prior Publication Data

US 2020/0390928 A1 Dec. 17, 2020

Related U.S. Application Data

(63) Continuation-in-part of application No. 15/964,849, filed on Apr. 27, 2018, now abandoned.

(51) Int. Cl.
*A62B 7/08* (2006.01)
*A24F 25/00* (2006.01)
*A61L 2/20* (2006.01)
*A61L 9/00* (2006.01)
*A61L 9/12* (2006.01)

(52) U.S. Cl.
CPC .................. *A61L 9/12* (2013.01); *A61L 2/20* (2013.01); *A61L 2209/133* (2013.01); *A61L 2209/134* (2013.01)

(58) Field of Classification Search
CPC . A61L 9/04; A61L 2209/133; A61L 2209/134
USPC .............................. 422/123, 306; 239/35, 56
See application file for complete search history.

(56) References Cited

U.S. PATENT DOCUMENTS

| | | | |
|---|---|---|---|
| 4,258,004 A | 3/1981 | Valenzona et al. | |
| 4,372,490 A * | 2/1983 | Le Caire, Jr. ............. | A61L 9/12 220/4.24 |
| 2014/0091487 A1 * | 4/2014 | Belongia ................. | A61L 9/122 261/146 |

\* cited by examiner

*Primary Examiner* — Monzer R Chorbaji
(74) *Attorney, Agent, or Firm* — Wood, Phillips, Katz, Clark & Mortimer

(57) ABSTRACT

A device which reduces odor in athletic apparel storage, notably athletic or "gym" bags, lockers, and similar places where athletic apparel might be stored before it can be washed is disclosed. An exterior configuration for the device making it simple to use and appropriate for use in rugged conditions is also disclosed, as is an improved embodiment making the mode of the device (active or inactive) readily apparent. A deodorizing cartridge which is easy and efficient to manufacture while allowing easy refilling and maintaining durability is also disclosed.

18 Claims, 6 Drawing Sheets

DEVICE FOR REDUCING ODOR IN ATHLETIC APPAREL STORAGE

PRIORITY CLAIM/CROSS REFERENCE TO RELATED APPLICATION AND INCORPORATION BY REFERENCE

This application claims priority to U.S. patent application Ser. No. 15/964,849, "DEVICE FOR REDUCING ODOR IN ATHLETIC APPAREL STORAGE," filed Apr. 27, 2018, in the United States Patent and Trademark Office, said application by the same inventive entity, with the entirety of said application being incorporated herein by reference to provide continuity of disclosure.

This invention relates to a device which neutralizes odor-causing compounds in athletic apparel storage, notably athletic or "gym" bags, lockers, closets and similar places where athletic apparel might be stored before it can be washed. The device uses chemical means both to reduce the odor of unwashed apparel by chemically neutralizing odor-causing compounds and to mask the odor of unwashed apparel with a preferable fragrance. The device is configured to allow it to be used in rough conditions and to be activated and deactivated by simple means. A novel case-and-cartridge configuration allows easy refilling while maintaining durability.

BACKGROUND OF THE INVENTION

Human beings have been participating in athletic events for thousands of years. For just as long, the problem of saturating garments with perspiration and the resultant odor has presented itself. (The Ancient Greeks simply participated in athletic events with no clothes at all, which is not practical in modern society.)

In modern times, the problem is compounded by the fact that many people perform exercise or other athletic activity at gyms, fitness centers, community parks, or other places where they must travel to the athletic activity in street clothes, change to athletic apparel, perform the activity, and change back into street clothes, and then transport the used athletic apparel in a gym bag, duffle, or other container before it can be washed. The result is that the apparel remains saturated with perspiration and cannot dry out, thereby increasing the production of perspiration-related odor. A device which could ameliorate the development of such odor will be a useful invention.

Further, athletic apparel and other equipment worn on the body is frequently packed in such containers with small weights, skates either wheeled or bladed, sticks of various kinds for playing various games, and so forth. This produces a very rough environment where any device for ameliorating the development of such odor will be subject to potential impacts, cuts, or other rough treatment. A device for ameliorating the development of such odor which can stand up to such rough treatment will be a useful invention.

Also, gyms and sporting events are very active locations, and sporting equipment and the bags it is kept in are often treated very harshly. The actual deodorizing materials used in deodorizing devices might be damaged or destroyed in such an environment before providing their benefits. A device for ameliorating odor able to protect the deodorizing materials from rough treatment and harsh environments will be a useful invention.

Finally, people in athletic environments are often in a rush and do not have time or inclination to perform complex or subtle operations when storing their equipment. A device which will ameliorate the development of such odor in a simple, easy and effective way will be a useful invention.

The present invention addresses these and other related concerns.

SUMMARY OF THE INVENTION

Among the many objectives of the present invention is the provision of a device which can ameliorate the development of perspiration-related odor in bags and other containers where athletic equipment is stored.

Another objective of the present invention is the provision of a device which can ameliorate the development of perspiration-related odor in athletic environments, where rough handling is a possibility, without being easily damaged.

Yet another objective of the present invention is the provision of a device which can ameliorate the development of perspiration-related odor and can be easily and visibly activated, deactivated, and refilled.

These and other objectives of the invention (which other objectives become clear by consideration of the specification and drawings as a whole) are met by providing the device for reducing odor in athletic apparel storage set forth in the specification hereof.

DESCRIPTION OF THE PREFERRED EMBODIMENTS

Reference will now be made in detail to several embodiments of the invention that are illustrated in accompanying drawings. Whenever possible, the same or similar reference numerals are used in the drawings and the description to refer to the same or like parts or steps. The drawings are in simplified form and are not to precise scale. For purposes of convenience and clarity only, directional terms such as top, bottom, left, right, up, over, above, below, beneath, rear, and front, may be used with respect to the drawings. These and similar directional terms are not to be construed to limit the scope of the invention in any manner. The words attach, connect, couple, and similar terms with their inflectional morphemes do not necessarily denote direct or intermediate connections, but may also include connections through mediate elements or devices.

For purposes of this application, there are two methods for remediating the odors associated with sweat, dirt, et cetera accumulated by athletic wear and equipment during exercise. The first method is to introduce a chemical which will chemically neutralize the odor-causing compounds, either by chemically reacting with them in such a way as to produce compounds which are not (as) odiferous, or by chemically bonding with them to prevent their dispersement and circulation through the air. Chemical neutralization of the actual odor-causing compounds by either method will be referred to herein as deodorizing with a deodorizer. The second method is to introduce a chemical with a pleasant scent which will mask, cover up, or otherwise distract from and/or overpower the scent of the odor-causing compounds. This will be referred to herein as masking odors with a masking scent. Any given substance used for purposes of the invention may be and/or contain a deodorizer, a masking scent, or both.

Figure 1:
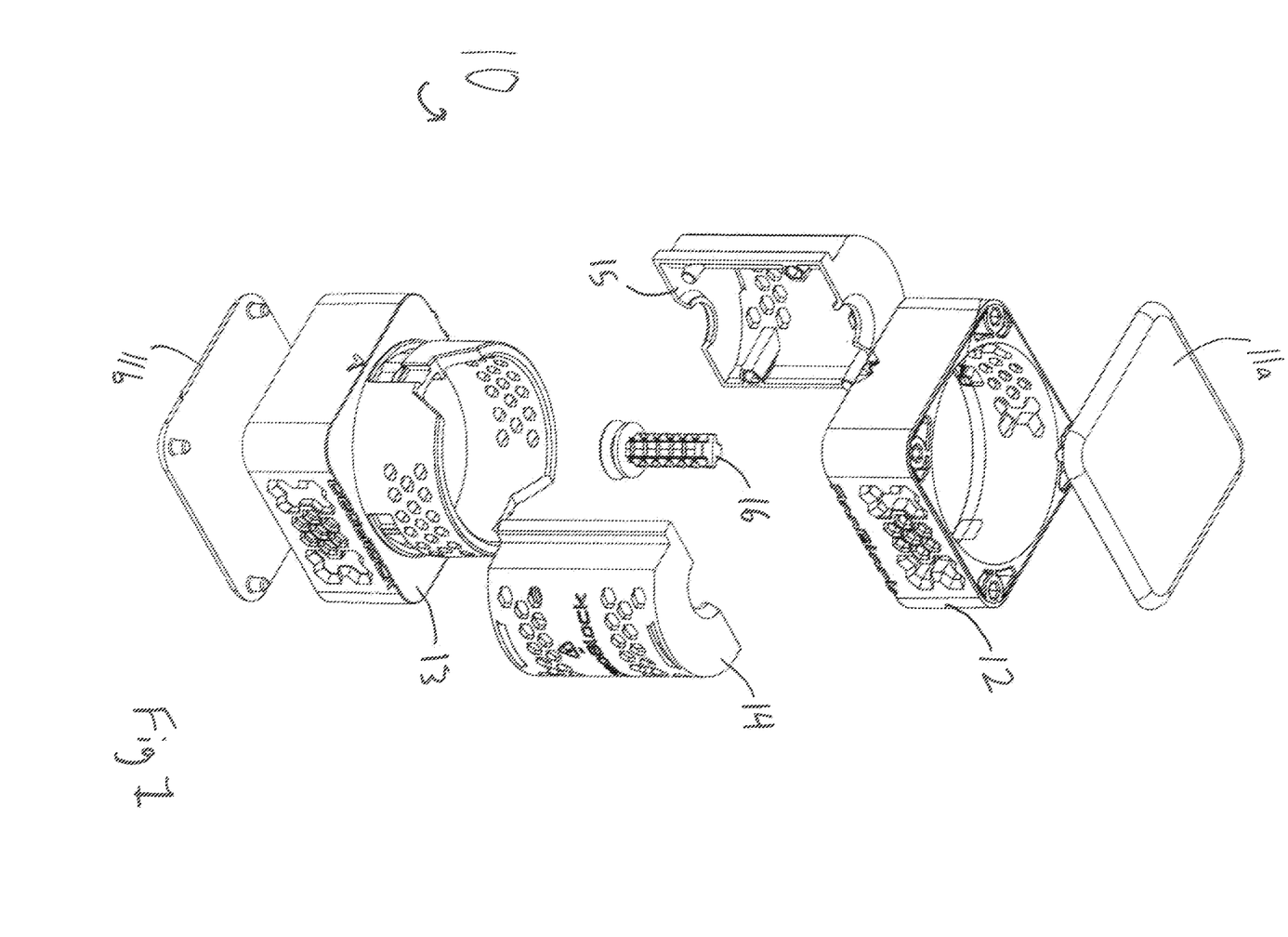
FIG. 1 depicts a perspective view of the preferred embodiment of the device.

By examining FIG. 1, the configuration and function of the invention may be clearly understood. Device 10 comprises, from top to bottom, top cap 11a, top 12, a deodorizing cartridge comprising first cartridge element 14 and second cartridge element 15 which together enclose deodorizing material stabilizer 16 and the deodorizing material (NOT SHOWN) bottom 13, and bottom cap 11b. When assembled, the vent holes in the exterior of device 10 either allow the interior of the deodorizing cartridge to communicate with the outside air (the device then said to be "activated,") or do not allow this (the device then said to be "deactivated.") When the device is activated, the deodorizing material performs its desired function and either masks odors in the vicinity, deodorizes air and objects in the vicinity, or both. When the device is deactivated, no such deodorizing or masking occurs. The function of each individual element of the device will be further explained below.

It should be noted that top cap 11a and bottom cap 11b are physically identical. It is optional, but neither preferred nor required, to have the caps be distinct, whether for decorative or other purposes. For instance, if the device has images corresponding to a licensed property or likeness, one cap may bear the likeness of an athlete, while the other cap has the team jersey number of that athlete and/or the logo of that athlete's team. It is also optional to use the cap configuration at all: if the cap configuration is not used, it is required that the ends of the top and the bottom which would have been closed by the caps be manufactured so that these ends are closed.

In FIG. 1, the device 10 is in an activated configuration. The faces of the device 10 which include vents are aligned, indicating that the device 10 is activated and that the vents are aligned with the corresponding vents in the deodorizing cartridge. The alignment indicators (see FIG. 2 and FIG. 3) are also aligned, indicating that the device 10 is both in the "activated" configuration for deodorizing, and that the top and bottom are locked together and cannot be separated because the top bosses are not aligned with the vertical channels (see FIG. 3.)

It is preferred, but not required, that the edges and corners of the device (both top 12 and bottom 14 and top cap 11a and bottom cap 11b) be slightly rounded so as to avoid scratching, ripping, or otherwise damaging the athletic apparel or equipment in the bag or other container, or the bag or other container itself. This also makes it less likely that the device 10 will catch on things and be damaged itself. It is strongly preferred, but not required, that the device 10 be cubical, as this provides surfaces which are easy to grip, easy to distinguish, and provide a simple way to positively identify and confirm the current configuration.

Figure 2:
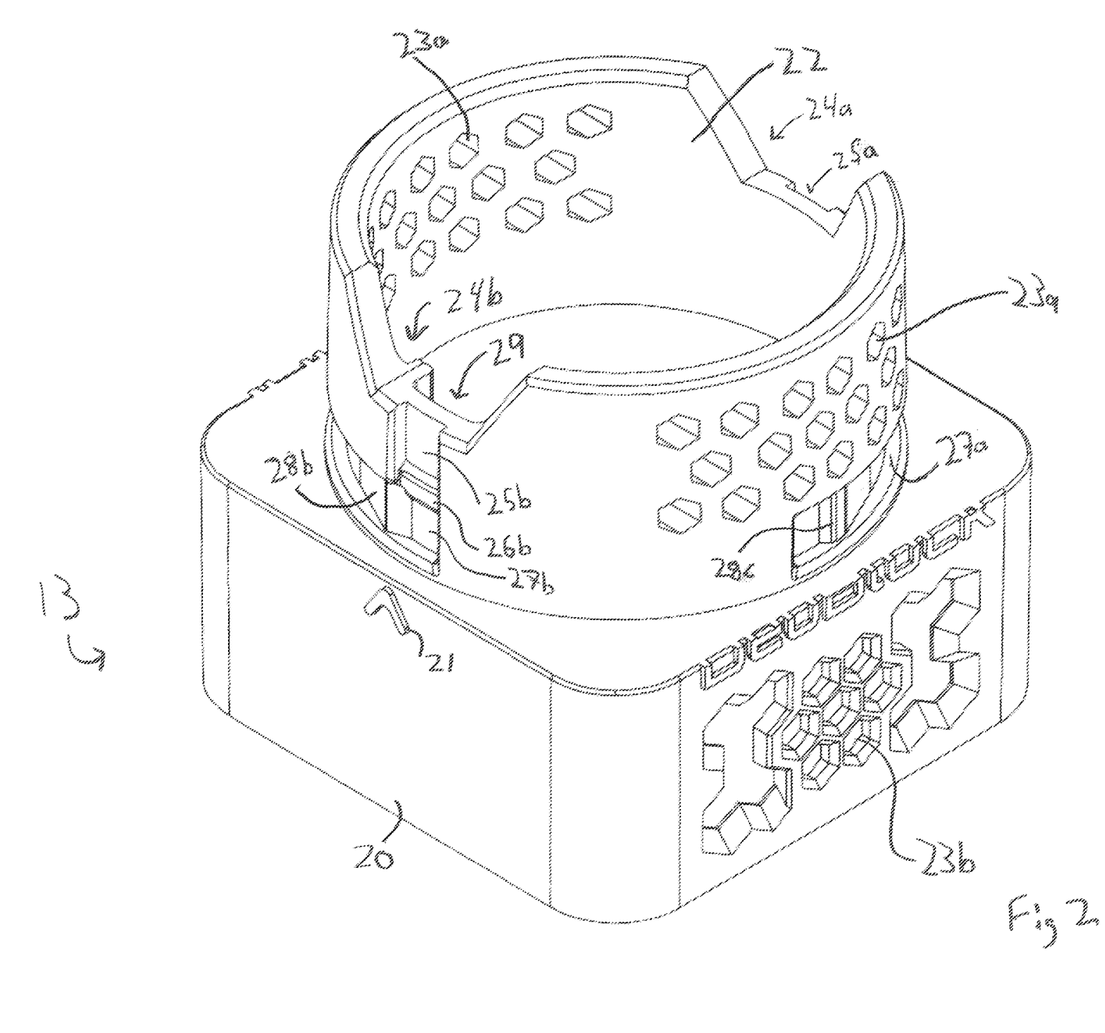
FIG. 2 depicts a perspective view of the bottom element of the device.

FIG. 2 shows the configuration of bottom 13. Bottom 13 comprises base 20 and vertical column 22. The exterior of base 20 is visible when the device is assembled, and vertical column 22 is inserted into cavity 34 of top 12 (see FIG. 3.)

Bottom interior vents 23a communicate with the interior of the device: when the device is activated, they will line up with vents 53a or vents 53b, depending on which way the deodorizing cartridge is inserted (see FIG. 5a) and top vents 33a, providing communication between the interior of the device where the deodorizing material is contained and the outside air. Bottom exterior vents 23b are blind vents which do not communicate with the interior of the device and are provided for reasons of visual symmetry. It is preferred that bottom exterior vents 23b be blind vents so that the device can be fully activated and fully deactivated by proper alignment of the top and bottom, but if it is desired for there to always be some communication between the interior of the device and the outside air, they can be through vents. This will result in less deodorizing activity when the device is in the "deactivated" alignment and more when it is in the "activated" alignment, but there will always be some deodorizing activity. It is optional to include bottom exterior vents at all.

Vertical column 22 includes cutouts 24a and 24b, the "notches" in the walls of the vertical column, which allow the user to more easily grip the deodorizing cartridge to remove it for refilling. (See FIG. 1.) It is strongly preferred to include some equivalent of the cutouts as otherwise it can be difficult to remove the deodorizing cartridge if it gets canted or debris gets between the interior of bottom 13 and the deodorizing cartridge and makes it difficult for the cartridge to slide out of the vertical column. On the interior of vertical column 22 is rail guide 29, a vertical channel which allows the rail formed when the deodorizing cartridge is assembled (see FIG. 5a-5c) to lock the deodorizing cartridge into position and stop it from rotating. It is required that there be some means for preventing the deodorizing cartridge from rotating with respect to base 13 so that the vents will all line up correctly when the device is activated or deactivated.

On the exterior of vertical column 22 are vertical channels 25a and 25b. Each vertical channel ends at a vertical boss 26 (26b is shown, 26a is not visible.) The vertical bosses partially interrupt the communication between the vertical channel and the horizontal channel. Below each vertical boss 26 is a horizontal channel 27 (27a and 27b respectively.) Proceeding to viewer left along each horizontal channel 27, each horizontal channel 27 is interrupted twice by first horizontal bosses 28a (not visible) and 28b, and second horizontal bosses 28c and 28d (not visible) leaving enough free space at the beginning of each horizontal channel and at the end of each horizontal channel for the corresponding top boss (NOT SHOWN, see FIG. 3) to interlock with the beginning or the end of the horizontal channel and the corresponding horizontal boss.

Both the vertical and the horizontal bosses interrupt, but do not completely block, the corresponding channels. It is required that the vertical and horizontal bosses leave enough clearance in the corresponding channels to allow the top bosses to clear them with the application of a reasonable amount of force by the user.

Bottom alignment indicator 21 is optional, but it or some equivalent is preferred. When bottom alignment indicator 21 is aligned with top alignment indicator 31 (see FIG. 3) the user knows both that the device is activated, and that the top and the base can not be separated for refilling purposes by pulling them apart and overcoming the friction/elastic resistance of top bosses 39a and 39b (not shown, see FIG. 3) against base vertical boss 26a and 26b (not shown.) When the bottom alignment indicator and the top alignment indicator are on tangent faces and not aligned, the user knows that the device is deactivated, and that the top and bottom can be separated for refilling purposes. Alternate methods of indicating alignment/activation status can also be used, such as corresponding colors or patterns on the faces which show when the device 10 is in a particular configuration. For instance, corresponding upper and lower halves of the word "DEOBLOCK" are visible on other faces of the device: when the word is complete, the user knows that the device is activated. Similar arrangements could be made to show deactivated status. Such indication is strongly preferred, but not required, as the user can always simply try to open the device 10 by using trial and error and/or closely inspect the vent holes to see if they are open to the interior of the device.

Figure 3:
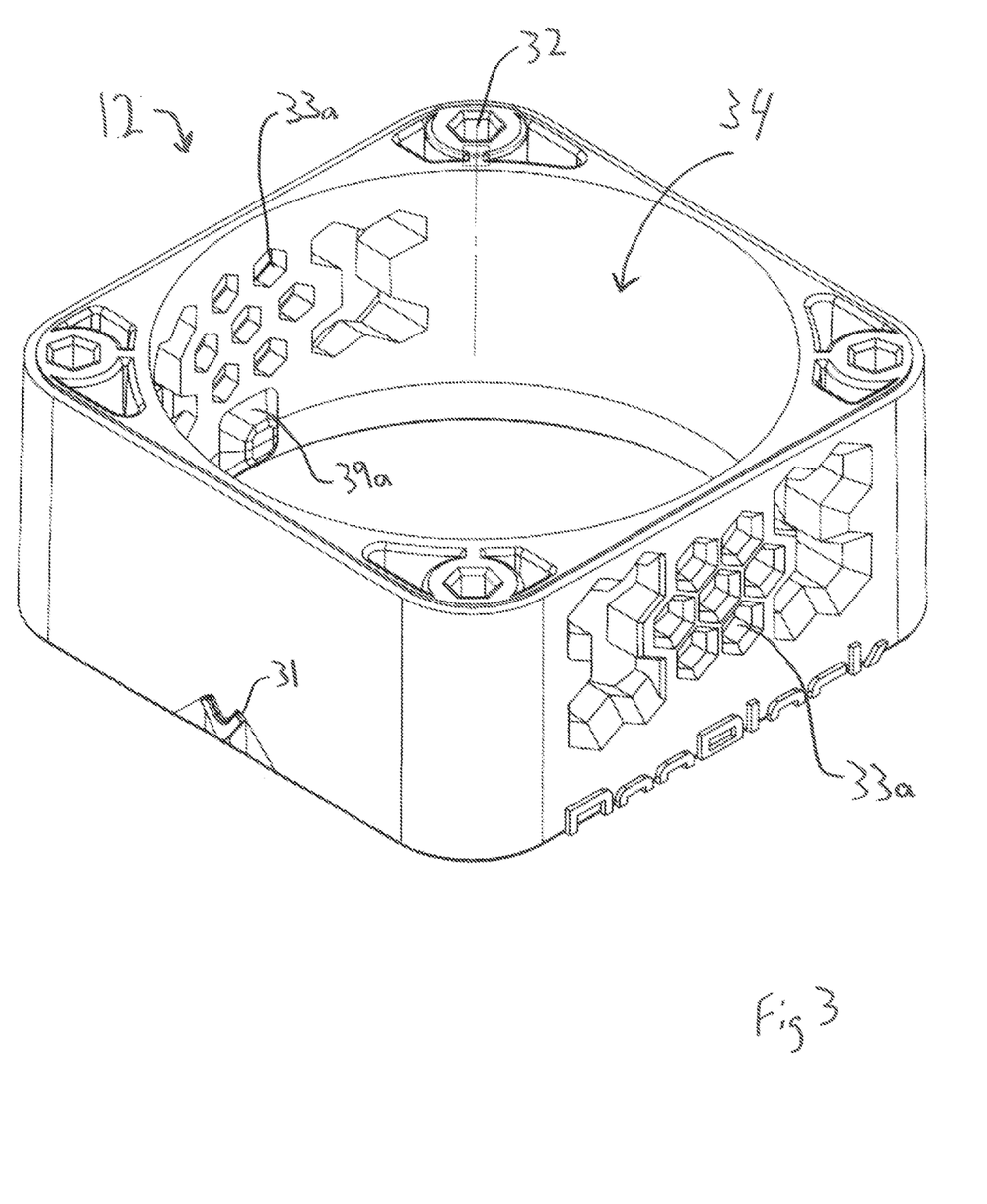
FIG. 3 depicts a perspective view of the top element of the device.

FIG. 3 shows the configuration of the top of the device. Top 12 has receivers 32 for pressure-fitted mounting elements of top cap 11a (see FIG. 1.) Top vents 33a allow the interior of the device to communicate with the external air. When the device is in the activated configuration, top vents 33a align with bottom interior vents 23a and vents 53 as previously described, allowing for deodorizing activity. When the device is in the deactivated configuration, top vents 33a do not so align, and there is no deodorizing activity (but see alternate configuration described above.) Vertical column 22 (see FIG. 2) is inserted into cavity 34 of top 12, and top 12 rotates relative to base 20 (see FIG. 2) with vertical column 22 serving as the "axle" of such rotation.

Top 12 has two top bosses 39 (top boss 39a is visible, top boss 39b, which is diametrically opposed to top boss 39a, is not.) To assemble the device, top 12 is aligned with bottom 13 such that cavity 34 can slide over vertical channel 22. Each top boss 39 is aligned with a vertical channel 25, so that each top boss can slide into the corresponding vertical channel. The first obstacle that the top bosses encounter are the corresponding vertical bosses: until the top bosses are slid past the vertical bosses by application of sufficient force on top 12, top 12 and bottom 13 can be easily separated. Once the top bosses are slid past the vertical bosses, the top and bottom are in a position corresponding to the "deactivated" configuration. The top will not easily separate or move vertically due to the interaction between the top boss and the vertical boss in each horizontal channel, and it will not easily turn to viewer left due to the interaction between the top boss and the first horizontal boss in each horizontal channel.

To activate the device, the top is rotated to viewer left relative to the bottom. Once past the first horizontal boss, the top boss will encounter the second horizontal boss in each horizontal channel. With sufficient torque, the user can rotate the top such that the top boss moves over and past the second horizontal boss, resulting in the top boss being trapped between the second horizontal boss and the end of the horizontal channel. This position corresponds to the "activated" configuration. The top will not move vertically as there is nowhere for the top boss to go, and it will not easily move horizontally due to the interaction between the top boss and the second horizontal boss in each horizontal channel. The vents in the top and bottom are aligned, allowing the deodorizing material to act on outside air as it flows in and out through the vents.

To deactivate the device, the top is rotated back to the position where the top bosses are at the other end of the horizontal channels, trapped between the first horizontal bosses and the ends of each horizontal channel. The vents are not aligned and outside air cannot flow in and out of the deodorizing cartridge, stopping the deodorizing process. Although the top can now be disengaged from the bottom, it will stay in the deactivated position unless sufficient force is applied to pull the top bosses over the vertical bosses.

Figure 4:
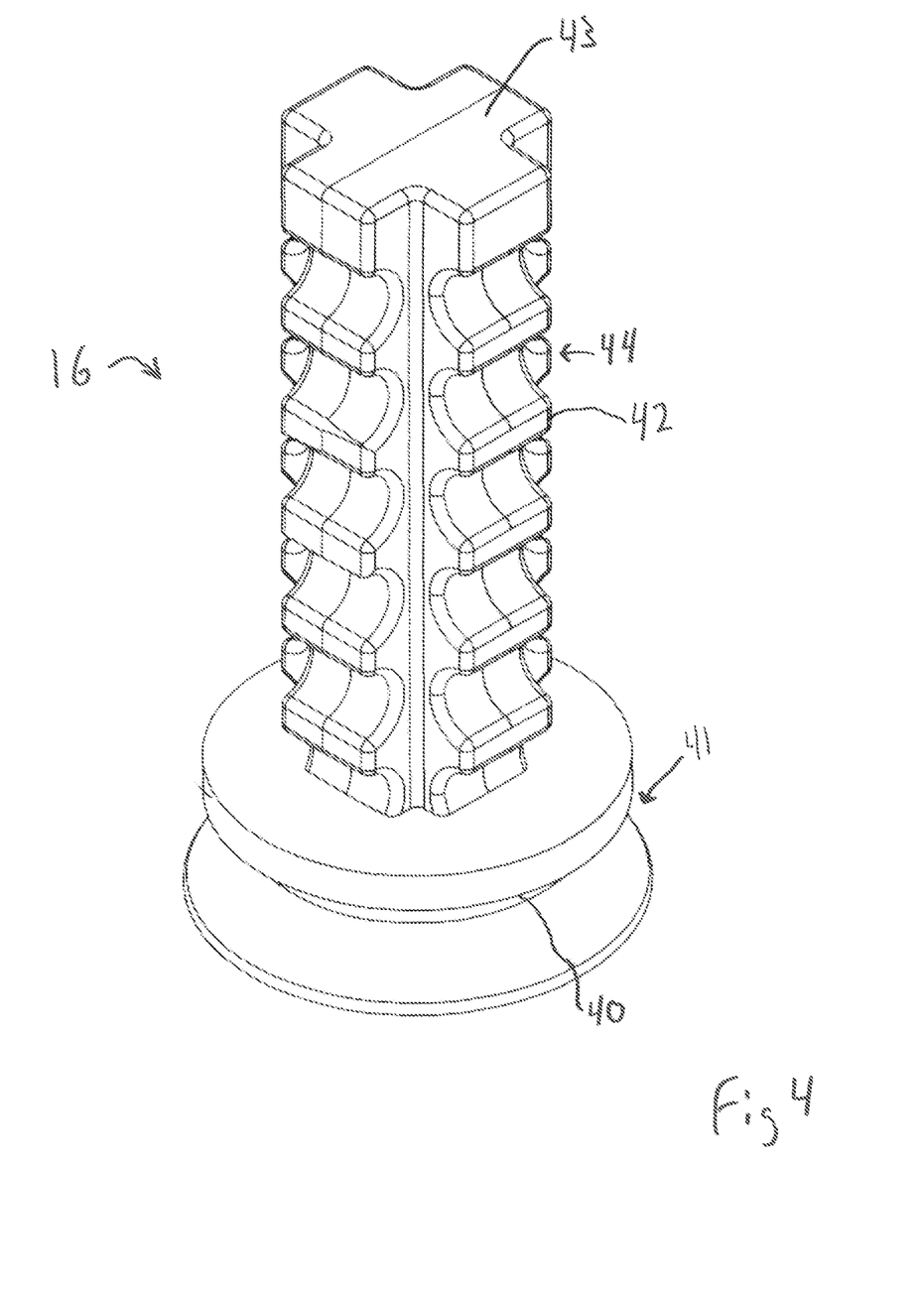
FIG. 4 depicts a perspective view of the deodorizing material stabilizer.

FIG. 4 shows the configuration of the deodorizing material stabilizer. In the preferred embodiment, the deodorizing material (not shown) is a gel, solid, or semi-solid material which fills or partially fills the deodorizing cartridge. If the deodorizing cartridge is simply partially or entirely filled with deodorizing material, the material can break loose (especially as such materials tend to shrink as they work) and may be broken into smaller and smaller pieces, some of which may escape through the vents, or block them and reduce the circulation of the air and hence the deodorizing activity. It is strongly preferred to use the deodorizing material stabilizer as shown to minimize the movement of the deodorizing material.

Deodorizing material stabilizer 16 consists of head 41 and shaft 43. Head 41 has groove 40 which engages flanges 55 (see FIG. 5a) of the deodorizing cartridge elements so that when the deodorizing cartridge is assembled, deodorizing material stabilizer 16 is locked into position. Along the shaft are ridges 42 which define cavities 44. When the deodorizing cartridge is filled, the ridges and cavities provide both additional surface area for engagement and a physical engagement which tends to retain the deodorizing material in place. It is strongly preferred to use ridges 42 or some equivalent thereof which are not continuous like a screw thread, which minimizes the opportunity for the deodorizing material to work its way loose.

It is preferred, but not required, that shaft 43 not be as long as the entire interior length of the deodorizing cartridge, to provide increased volume for deodorizing material.

Figure 5A:
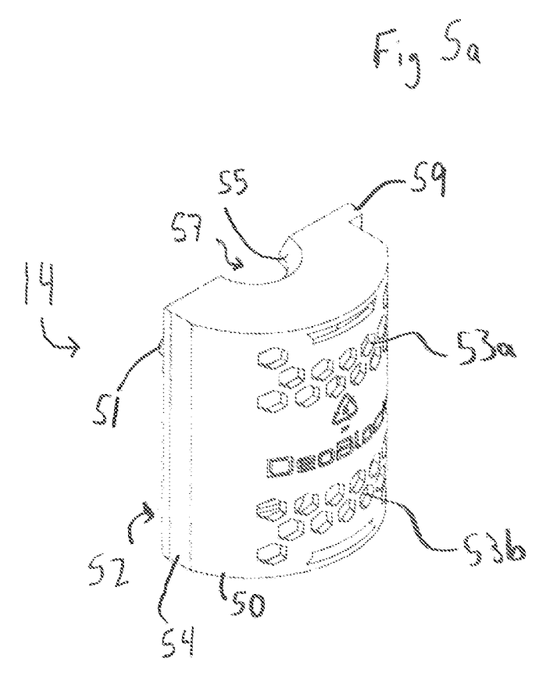
FIG. 5a depicts a perspective view of the first element of the deodorizing cartridge.

FIG. 5a shows the first cartridge element 14. It should be noted that in the preferred embodiment, the cartridge elements are mirror images of each other but otherwise identical for purposes of this application. This does not apply to non-functional features such as decoration or indicator markings. Optional flat area 54 allows an easier grip when the deodorizing cartridge is to be removed for refilling or replacement. Main portion 50 is cylindrically shaped and fits into the interior of vertical column 22 and cavity 34 such that top 12 can freely rotate and tightly interface with bottom 13. It is strongly preferred that the length of the cartridge elements is the same as the interior length of vertical column 22 such that the deodorizing cartridge cannot move vertically when the device is assembled.

Cartridge element bosses 51 interact with cartridge element boss receivers 52 (see FIG. 5b) such that the cartridge elements can be press-fitted together and forced into symmetrical alignment. Vents 53a and 53b communicate between the interior and exterior of the deodorizing cartridge such that the external air can circulate around the deodorizing material when all of the vents are aligned (in the "activated" configuration) so that deodorizing activity will occur. While it is optional to include vents 53b, it is preferred to include both so that no matter which way the deodorizing cartridge is inserted, the vents will align when the device is activated. If vents 53b are not included it is required that the deodorizing cartridge be inserted such that vents 53a are aligned with bottom interior vents 23a when the device is activated.

End openings 57 are defined and surrounded by flanges 55. One end opening will be filled by the head of the deodorizing material stabilizer (see FIG. 4.) The other will be open, but if the deodorizing cartridge is configured as described in the preferred embodiment, it will be sealed by the corresponding cap (see FIG. 1.)

Rail boss 59 forms the rail (along with the corresponding rail boss on the second cartridge element) which goes into rail channel 29 to keep the deodorizing cartridge aligned and locked into position.

It is strongly preferred, but not required, that the exterior corners of the rail be tangent to the circle defined by the exterior of the main portion of the deodorizing cartridge. If the deodorizing cartridge sleeve (see FIG. 6) is to be used, it is required that the exterior corners of the rail either be tangent to the circle defined by the exterior of the main portion of the deodorizing cartridge or be located inside it so that the deodorizing cartridge sleeve fits properly.

Figure 5B:
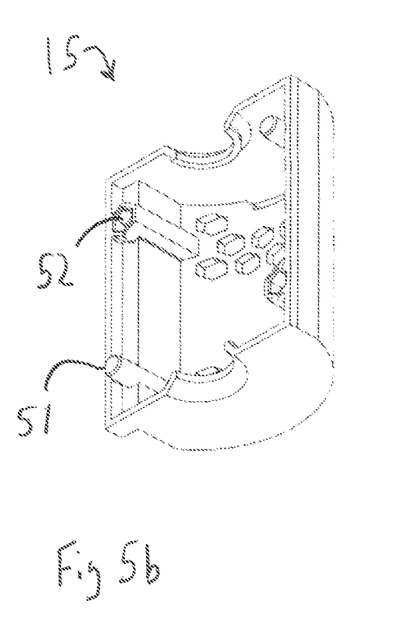
FIG. 5b depicts a cutaway perspective view of the second element of the deodorizing cartridge.

FIG. 5*b* shows the configuration of the cartridge element bosses and cartridge element boss receivers. Second cartridge element has cartridge element boss 51 which engages the corresponding cartridge element boss receiver on the first cartridge element, and cartridge element boss receiver 52 which engages the corresponding cartridge element boss on the first cartridge element. It is preferred, but not required, that the cartridge element bosses and cartridge element boss receivers be symmetrically distributed as shown.

Figure 5C:
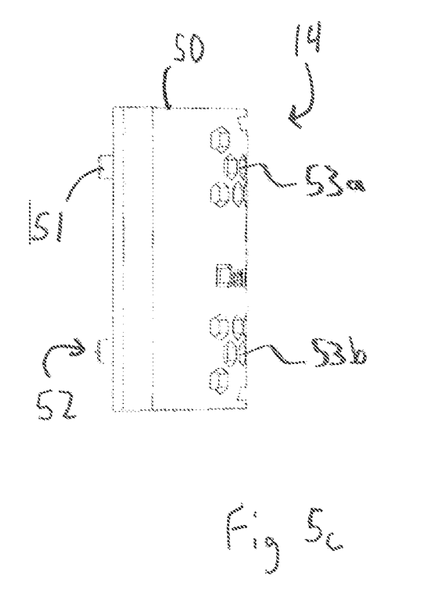
FIG. 5c depicts a side view of the first element of the deodorizing cartridge.

FIG. 5*c* shows an alternate view of the first cartridge element, with the vents 53*a* and 53*b*, main portion 50, cartridge element boss 51, and cartridge element boss receiver 52 (not visible.)

Figure 6:
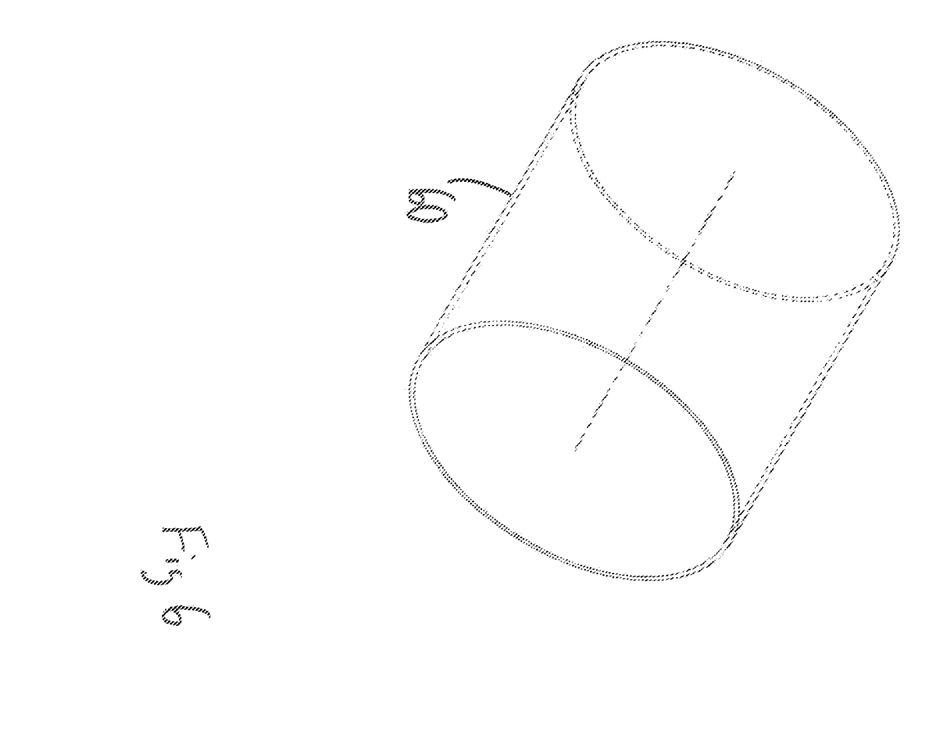
FIG. 6 depicts a perspective view of the deodorizing cartridge sleeve.

FIG. 6 is an optional deodorizing cartridge sleeve. In the preferred embodiment, the deodorizing material stabilizer is inserted between the deodorizing cartridge elements such that the head of the deodorizing material stabilizer blocks one end opening. Sleeve 60 is the same length as the assembled deodorizing cartridge and has an interior diameter the same size as the exterior diameter of the main portion of the deodorizing cartridge. The deodorizing cartridge is placed within sleeve 60 and the deodorizing material, in liquid or semi-liquid form, is inserted into the deodorizing cartridge through the other end opening. The deodorizing material cannot escape through the vents as they are blocked by the sleeve. Once the deodorizing cartridge is filled to the desired level, the entire assembly is shrink-wrapped, taped, or otherwise secured so that the deodorizing material cannot escape if the device is tilted and the sleeve will not slide off the deodorizing cartridge until the device is ready for use. Before that time, the deodorizing material will harden to the point where it will not flow out of the vents or the open end of the deodorizing cartridge. When the device is ready for use, the user simply removes the seal and the sleeve, inserts the deodorizing cartridge into the device, and activates it.

While various embodiments and aspects of the present invention have been described above, it should be understood that they have been presented by way of example only, and not limitation. Thus, the breadth and scope of the present invention should not be limited by any of the above exemplary embodiments.

This application—taken as a whole with the abstract, specification, and drawings being combined—provides sufficient information for a person having ordinary skill in the art to practice the invention as disclosed herein. Any measures necessary to practice this invention are well within the skill of a person having ordinary skill in this art after that person has made a careful study of this disclosure.

Because of this disclosure and solely because of this disclosure, modification of this device and method can become clear to a person having ordinary skill in this particular art. Such modifications are clearly covered by this disclosure.

What is claimed and sought to be protected by Letters Patent is:

1. A device for reducing odor in athletic apparel storage comprising:
   a) A top piece having a top interior cavity having an interior circumference, a first vent allowing the top interior cavity to communicate with an external atmosphere, and at least one top boss, all of the at least one top bosses dispersed around a lower edge of the interior circumference;
   b) A bottom piece having a base portion and an extending column portion having an exterior column wall and a bottom interior cavity, the extending column portion having a second vent allowing the bottom interior cavity to communicate with the external atmosphere, such that the top piece can be operably attached to the bottom piece by inserting the extending column portion into the top interior cavity through the interior circumference;
   c) At least one vertical channel in the exterior column wall such that for each of the at least one top bosses, there is a corresponding vertical channel, the at least one vertical channels disposed about the exterior column wall such that the corresponding top bosses can all simultaneously enter the corresponding vertical channels;
   d) At least one vertical boss, such that one of the at least one vertical bosses is present in each of the at least one vertical channels, the vertical boss partially obstructing the travel of the corresponding top boss such that the corresponding top boss will not move past the corresponding vertical boss in each of the at least one vertical channels without application of a first force by a user;
   e) At least one horizontal channel in the exterior column wall such that for each of the at least one vertical channels, there is a corresponding horizontal channel, the corresponding horizontal channels disposed about the exterior column wall such that the corresponding top bosses can all simultaneously enter the corresponding horizontal channels after the corresponding top bosses move past the corresponding vertical bosses, and each horizontal channel having a first end aligned with the corresponding vertical channel and a second end circumferentially disposed from the second end along the exterior column wall;
   f) At least one first horizontal boss, such that one of the at least one first horizontal bosses is present in each of the at least one horizontal channels, the first horizontal boss partially obstructing the travel of the corresponding top boss such that the corresponding top boss will not move past the corresponding first horizontal boss in each of the at least one horizontal channels without application of a second force by the user, each of the at least one first horizontal bosses preventing the corresponding top boss from moving out of alignment with the corresponding vertical channel until the second force is applied by the user;
   g) At least one second horizontal boss, such that one of the at least one second horizontal bosses is present in each of the at least one horizontal channels, the second horizontal boss partially obstructing the travel of the corresponding top boss such that the corresponding top boss will not move past the corresponding second horizontal boss in each of the at least one horizontal channels without application of a third force by the user, each of the at least one horizontal bosses preventing the corresponding top boss from moving out of alignment with the corresponding vertical channel until the third force is applied by the user, and each of the at least one second horizontal bosses defining a captive position wherein once the corresponding top boss moves past the corresponding second horizontal boss, the corresponding top boss is captive in the captive position between the corresponding second horizontal boss and the second end of the corresponding horizontal channel; and, h) A deodorizing cartridge contained within the bottom interior cavity.

2. A device for reducing odor in athletic apparel storage as in claim 1 wherein the first vent is not aligned with the second vent when each of the at least one top bosses is aligned with one of the at least one vertical channels such that the bottom interior cavity cannot communicate with the external atmosphere, and wherein the first vent is aligned with the second vent when each of the at least one top bosses is in the captive position such that the bottom interior cavity can communicate with the external atmosphere.

3. A device for reducing odor in athletic apparel storage as in claim 2 further comprising:
   i) A top alignment indicator on the top piece; and,
   j) A bottom alignment indicator on the bottom piece, such that when each of the at least one top bosses are in the captive position in the corresponding horizontal channel, the top alignment indicator is aligned with the bottom alignment indicator, indicating to the user that the first vent is aligned with the second vent and the bottom interior cavity is in communication with the external atmosphere.

4. A device for reducing odor in athletic apparel storage as in claim 1 further comprising:
   i) A top alignment indicator on the top piece; and,
   j) A bottom alignment indicator on the bottom piece, such that when the first vent is aligned with the second vent, the top alignment indicator is aligned with the bottom indicator, indicating to the user that the bottom interior cavity is in communication with the external atmosphere.

5. A device for reducing odor in athletic apparel storage as in claim 4 further comprising:
   k) A deodorizing material, the deodorizing material comprising a deodorizing gel material or a deodorizing semi-solid material, the deodorizing material contained within a deodorizing material cavity of the deodorizing cartridge; and,
   l) At least one deodorizing cartridge vent, the at least one deodorizing cartridge vent allowing the deodorizing material cavity to communicate with the second vent when the deodorizing cartridge is within the bottom interior cavity.

6. A device for reducing odor in athletic apparel storage as in claim 5 further comprising:
   m) A first deodorizing cartridge half having a first filling opening, a first deodorizing material stabilizer retaining opening, and a first deodorizing cartridge vent which is one of the at least one deodorizing cartridge vents;
   n) A second deodorizing cartridge half having a second filling opening, a second deodorizing material stabilizer retaining opening, and a second deodorizing cartridge vent which is one of the at least one deodorizing cartridge vents, the first deodorizing cartridge half and the second deodorizing cartridge half forming the deodorizing cartridge when the first deodorizing cartridge half is tangent to the second deodorizing cartridge with the first filling opening aligned with the second filling opening to define a deodorizing cartridge filling opening and the first deodorizing material stabilizer retaining opening is aligned with the second deodorizing material stabilizer opening to form a deodorizing cartridge stabilizer opening; and,
   o) A deodorizing material stabilizer, the deodorizing material stabilizer having a shaft having a plurality of ridges defining a plurality of gaps, the shaft located within the deodorizing material cavity such that the deodorizing material is stabilized by adherence to and/or mechanical interlocking with and/or frictional interaction with the plurality of ridges, the deodorizing material stabilizer also having a head which can be captured within the deodorizing material stabilizer opening.

7. A device for reducing odor in athletic apparel storage as in claim 6 further comprising:
   p) A first key member on the first deodorizing cartridge half;
   q) A second key member on the second deodorizing cartridge half; and,
   r) A key slot in the bottom interior cavity such that when the deodorizing cartridge is placed within the bottom interior cavity, the first key member and the second key member are captive within the key slot.

8. A device for reducing odor in athletic apparel storage as in claim 7 further comprising:
   s) a removable filling sleeve which can be removably placed around the deodorizing cartridge once the first deodorizing cartridge half is tangent to and aligned with the second deodorizing cartridge half to form the deodorizing cartridge, such that the removable filling sleeve blocks the first deodorizing cartridge vent and the second deodorizing cartridge vent when placed about the deodorizing cartridge, and further such that when the removable filling sleeve is placed about the deodorizing cartridge and the head is captured within the deodorizing material stabilizer opening, only the deodorizing cartridge filling opening is not blocked by either the removable filling sleeve or the head.

9. A device for reducing odor in athletic apparel storage as in claim 5 further comprising:
   m) a removable filling sleeve which can be removably placed about the deodorizing cartridge, the removable filling sleeve blocking all of the at least one deodorizing cartridge vents when placed about the deodorizing cartridge.

10. A device for reducing odor in athletic apparel storage as in claim 1, further comprising:
    i) A deodorizing material, the deodorizing material comprising a deodorizing gel material or a deodorizing semi-solid material, the deodorizing material contained within a deodorizing material cavity of the deodorizing cartridge; and,
    j) At least one deodorizing cartridge vent, the at least one deodorizing cartridge vent allowing the deodorizing material cavity to communicate with the second vent when the deodorizing cartridge is within the bottom interior cavity.

11. A device for reducing odor in athletic apparel storage as in claim 10, further comprising:
    k) A deodorizing material stabilizer, the deodorizing material stabilizer having a shaft having a plurality of ridges defining a plurality of gaps, the shaft located within the deodorizing material cavity such that the deodorizing material is stabilized by adherence to and/or frictional interaction with the plurality of ridges.

12. A device for reducing odor in athletic apparel storage as in claim 11, wherein the gaps are noncontiguous.

13. A device for reducing odor in athletic apparel storage as in claim 10, further comprising:
   k) A first deodorizing cartridge half having a first filling opening, a first deodorizing material stabilizer retaining opening, and a first deodorizing cartridge vent which is one of the at least one deodorizing cartridge vents;
   l) A second deodorizing cartridge half having a second filling opening, a second deodorizing material stabilizer retaining opening, and a second deodorizing cartridge vent which is one of the at least one deodorizing cartridge vents, the first deodorizing cartridge half and the second deodorizing cartridge half forming the deodorizing cartridge when the first deodorizing cartridge half is tangent to the second deodorizing cartridge with the first filling opening aligned with the second filling opening to define a deodorizing cartridge filling opening and the first deodorizing material stabilizer retaining opening is aligned with the second deodorizing material stabilizer opening to form a deodorizing cartridge stabilizer opening; and,
   m) A deodorizing material stabilizer, the deodorizing material stabilizer having a shaft having a plurality of ridges defining a plurality of gaps, the shaft located within the deodorizing material cavity such that the deodorizing material is stabilized by adherence to and/or and or mechanical interlocking with and/or frictional interaction with the plurality of ridges, the deodorizing material stabilizer also having a head which can be captured within the deodorizing material stabilizer opening.

14. A device for reducing odor in athletic apparel storage as in claim 13, further comprising:
   n) a removable filling sleeve which can be removably placed around the deodorizing cartridge once the first deodorizing cartridge half is tangent to and aligned with the second deodorizing cartridge half to form the deodorizing cartridge, such that the removable filling sleeve blocks the first deodorizing cartridge vent and the second deodorizing cartridge vent when placed about the deodorizing cartridge, and further such that when the removable filling sleeve is placed about the deodorizing cartridge and the head is captured within the deodorizing material stabilizer opening, the deodorizing material cavity's only opening is the deodorizing cartridge filling opening.

15. A device for reducing odor in athletic apparel storage as in claim 13 further comprising:
   n) A first key member on the first deodorizing cartridge half;
   o) A second key member on the second deodorizing cartridge half; and,
   p) A key slot in the bottom interior cavity such that when the deodorizing cartridge is placed within the bottom interior cavity, the first key member and the second key member are captive within the key slot.

16. A device for reducing odor in athletic apparel storage as in claim 15 wherein the second vent is aligned with the deodorizing cartridge vent when the first key member and the second key member are in the key slot, but the first vent is not aligned with the second vent when each of the at least one top bosses is aligned with one of the at least one vertical channels such that the bottom interior cavity cannot communicate with the external atmosphere, and wherein the first vent is aligned with the second vent when each of the at least one top bosses is in the captive position such that the bottom interior cavity can communicate with the external atmosphere.

17. A device for reducing odor in athletic apparel storage as in claim 10, further comprising:
   k) a removable filling sleeve which can be removably placed about the deodorizing cartridge, the removable filling sleeve blocking all of the at least one deodorizing cartridge vents when placed about the deodorizing cartridge.

18. A device for reducing odor in athletic apparel storage as in claim 10 wherein the second vent is always aligned with the deodorizing cartridge vent, but the first vent is not aligned with the second vent when each of the at least one top bosses is aligned with one of the at least one vertical channels such that the bottom interior cavity cannot communicate with the external atmosphere, and wherein the first vent is aligned with the second vent when each of the at least one top bosses is in the captive position such that the bottom interior cavity can communicate with the external atmosphere.

* * * * *